United States Patent [19]
Barnett et al.

[11] Patent Number: 5,416,102
[45] Date of Patent: May 16, 1995

[54] METHOD OF PREVENTING THE REINFESTATION OF DOGS AND CATS BY FLEAS

[75] Inventors: Sharron H. Barnett, Greensboro; Roland H. Johnson; Douglas I. Hepler, both of High Point, all of N.C.; Manfred Böger, Weil am Rein, Germany

[73] Assignee: Ciba-Geigy Corporation, Ardsley, N.Y.

[21] Appl. No.: 266,153

[22] Filed: Jun. 27, 1994

Related U.S. Application Data

[63] Continuation of Ser. No. 982,231, Nov. 25, 1992, abandoned, which is a continuation of Ser. No. 502,805, Apr. 2, 1990, abandoned, which is a continuation-in-part of Ser. No. 893,763, Aug. 6, 1986, abandoned, and a continuation-in-part of Ser. No. 310,257, Feb. 13, 1989, Pat. No. 4,973,589, and a continuation-in-part of Ser. No. 476,109, Jan. 30, 1990, abandoned, said Ser. No. 310,257, is a continuation-in-part of Ser. No. 893,763, Jan. 30, 1990, said Ser. No. 476,109, is a continuation-in-part of Ser. No. 190,797, May 6, 1988, abandoned, which is a continuation of Ser. No. 38,684, Apr. 15, 1987, abandoned, which is a continuation of Ser. No. 820,814, Jan. 17, 1984, Pat. No. 4,677,127, which is a continuation of Ser. No. 613,538, May 24, 1984, abandoned, which is a continuation of Ser. No. 439,545, Nov. 5, 1982, abandoned.

[30] Foreign Application Priority Data

Nov. 10, 1981 [CH] Switzerland ............. 7208/81
Oct. 8, 1982 [CH] Switzerland ............. 5925182

[51] Int. Cl.$^6$ .................... A01N 43/40; A01N 47/28
[52] U.S. Cl. ........................... 514/351; 514/594
[58] Field of Search ........................ 514/351, 594

[56] References Cited

U.S. PATENT DOCUMENTS

| | | | |
|---|---|---|---|
| 3,962,458 | 6/1976 | Schrider | 424/304 |
| 4,089,975 | 5/1978 | Wade et al. | 424/322 |
| 4,139,636 | 2/1979 | Sirrenberg et al. | 424/322 |
| 4,234,600 | 11/1980 | Sirrenberg et al. | 424/310 |
| 4,310,530 | 1/1982 | Nishiyama et al. | 424/263 |
| 4,321,276 | 3/1982 | Ehrenfreund et al. | 424/322 |
| 4,350,706 | 9/1982 | Brouwer et al. | 424/322 |
| 4,399,152 | 8/1983 | Brouwer et al. | 424/322 |
| 4,405,552 | 9/1983 | Miesel | 424/263 |
| 4,518,804 | 5/1985 | Rigterink et al. | 564/442 |

FOREIGN PATENT DOCUMENTS 0008540 3/1980 European Pat. Off. .

*Primary Examiner*—Allen J. Robinson
*Attorney, Agent, or Firm*—Bruce M. Collins; Edward McC. Roberts

[57] ABSTRACT

A method of treating fleas on dogs and cats by orally administering a larvicidally or ovicidally effective amount of flea growth inhibiting benzoylurea.

26 Claims, No Drawings

METHOD OF PREVENTING THE REINFESTATION OF DOGS AND CATS BY FLEAS

CROSS REFERENCE TO RELATED APPLICATIONS

This is a continuation of Ser. No. 07/982,231, filed Nov. 25, 1992, now abandoned, which in turn is a continuation of Ser. No. 07/502,805, filed Apr. 2, 1990, now abandoned, which in turn is a continuation-in-part of (i) Ser. No. 06/893,763, filed Aug. 6, 1986, now abandoned, (ii) Ser. No. 07/310,257, filed Feb. 13, 1989, now U.S. Pat. No. 4,973,589, and (iii) Ser. No. 07/476,109, filed Jan. 30, 1990, now abandoned. Ser. No. 07/310,257 is a continuation-in-part of Ser. No. 06/893,763 and Ser. No. 07/476,109 is a continuation-in-part of Ser. No. 07/190,797, filed May 6, 1988, now abandoned, which in turn is a continuation of Ser. No. 07/038,684, filed Apr. 15, 1987, now abandoned, which in turn is a continuation of Ser. No. 06/820,814, filed Jan. 17, 1986, now U.S. Pat. No. 4,677,127, which in turn is a continuation of Ser. No. 06/613,538, filed May 24, 1984, now abandoned, which in turn is a continuation of Ser. No. 06/439,545, filed Nov. 5, 1982, now abandoned.

BACKGROUND OF THE INVENTION

Blood sucking parasitic infestation on animals, especially the infestation of pets by fleas, has been a continued problem in the art. On account of the complexity of the life cycle of the flea, none of the methods known to the prior art of controlling such parasites is entirely satisfactory, especially since these methods are directed primarily to the control of adult fleas in the coat of the host animal and do not take into account the different juvenile stages of the fleas existing in the animals coats as well as on the floor, on carpets, in bedding, on chairs, in the garden and in other places with which the infested animal usually comes into contact. Adult cat and dog fleas (*Ctenocephalides felis* and *C. canis*) live naturally in the coat of the cat or dog host. They feed on host blood and the females lay eggs in the coat. Since the eggs are not sticky, they quickly fall off and can be found on the floor, carpets, animals' beddings, chairs used by the pets, the garden, the backyard, etc.

Thus, the total environment of the animal is infested with flea eggs, which in about two days hatch into larvae. There are three larval stages, each lasting about three days. In the last stage the larvae spin cocoons and transform to pupae. Under optimum conditions, i.e., 33° C. and 65% relative humidity, the eggs transform to pupae in about 8 to 10 days. After a further period of approximately 8 days, the pupae develop to young adult fleas in the cocoon still lying on the floor, the carpets, the beddings, the chairs, etc. The young adult fleas wait until they sense the presence of an acceptable host animal and then emerge and attempt to jump onto it. Thus, it takes at least three weeks for eggs to develop to young adults able to reinfest the host. However, the young adults can remain for months, possibly as long as one year, in the cocoon, and in addition, under suboptimum conditions, it can take 4 to 5 months for the eggs to develop into young adults. Fleas must have a blood meal in order to become sexually mature and therefore be able to reproduce. The blood must come from the correct type of host.

This long life cycle, occurring at sites other than on the animal, has important implications for flea treatment applied to host animals. Even if fleas in the coat of the animal can be controlled successfully, i.e., if all adult fleas are killed by an active ingredient, the cat or dog is nevertheless exposed for weeks or even months to the risk of reinfestation by the newly emerged adults present in the animal's environment.

Infestation of dogs and cats with fleas has several undesirable effects for the treated animals or the owner. Such undesirable effects may manifest themselves in the form of local irritation or annoying itching, often leading to scratching. Quite a high number of animals become allergic to flea saliva, resulting in very itchy and crusty lumps on the animal's body at the site of the bites. Normally these lumps reach a diameter of 3 mm or more and cause the animal to bite and scratch, leading to subsequent hair loss. The infested animals create a nervous reaction and become more and more unattractive and irritable.

Furthermore, animals which are infested by fleas are permanently exposed to the danger of being infected by Dipylidium, a tape worm which is transmitted by the fleas.

Flea infestation not only is extremely annoying for the infested animal, but also unpleasant for the owner who observes the unusual behavior of a pet which is ill, suffering, and in need of help. In the prolonged absence of a suitable host animal, newly hatched fleas on the floor are compelled to attack humans (although they are not capable of reproduction if human blood is their sole source of nutrition). Even in the presence of the dog or cat, the owner may be bitten by the fleas. Moreover, some humans may suffer from allergic skin diseases as a result of dog and cat fleas or their excretes.

A number of methods for the control of fleas are known, but these have various drawbacks. When using flea combs for example, the animal owner has no choice other than combing the animal intensively and frequently. Depending on the size of the animal, this may take from several minutes to an hour. Not every animal will always patiently put up with being combed, nor is every owner prepared to sacrifice his time for this operation.

The use of anti-flea shampoos in many cases is impossible since most cats and a large number of dogs simply refuse to be given a bath or they can only be given a bath when the owner resorts to using force, in which case water and shampoo will be splashed about. Furthermore, the effect of such bathing does not last for more than about a week and the laborious procedure then must be repeated. Similar problems are encountered when using dips or rinses. Even the use of dusting powders as a rule is not tolerated by the animal without resistance since it takes several minutes to treat the entire surface of the coat uniformly and some dust is bound to get into the mouth, nose, and eyes of the animal. Even in the case of careful application, it is impossible to prevent the powder from being inhaled by the animal or its owner. There is virtually no way for the owner to avoid a more or less intensive contact with the active ingredient.

When using sprays, an owner may experience an unpleasant surprise since most animals, particularly cats, take flight or react aggressively to the noise of the spray. Moreover, sprays have all the drawbacks mentioned above for powders and, in addition, they disperse even more finely in the atmosphere, which means that animals and their owners simply can not avoid inhaling them.

Fleas are frequently also controlled with flea collars which are very effective temporarily. A particular weakness of this method of treatment, however, is that it is normally effective in a very limited region of the animal's body. In general, 100% kill is achieved in the region of the neck and thorax; however, more remote parts of the body are hardly affected. Besides, many of these collars look unattractive and may also irritate the animal. Today medallions are available which can be attached to the collar and which are said to be active. These medallions are appealing to the eye, but their effectiveness is unsatisfactory since they do not come into sufficient contact with the animal's coat. Several anti-flea organophosphorus compounds are available in the form of spot-on formulations. These are applied to a limited spot on the coat. In general, they exhibit good short-term activity against adult fleas but when applied often, the compositions have problematic toxicity. Some organophosphorus compounds are administered orally but have narrow safety limits and must never be applied simultaneously with other organophosphorus compounds.

On the whole it can be said that it has always been the objective of previous methods to kill the adult flea. Some of these methods can be applied quite successfully to control adult fleas for a short period. A fact which has so far not been acknowledged is that, owing to the particular life cycle of fleas, dogs and cats will be repeatedly reinfested because, on the one hand, the animal can not avoid coming into contact with the flea eggs, flea larvae and juvenile and adult fleas on the floor or in its immediate vicinity and, on the other hand, many pets again and again come into contact with infested members of the same species. Constantly recurring reinfestation is not prevented by using conventional pesticides.

DETAILED DESCRIPTION OF THE INVENTION

Surprisingly, it has been found that by specific modes of application and by using benzoylureas which block the development of juvenile flea stages, the vicious circle of constantly recurring reinfestation, described above in detail, can be brought to an end in simple manner, thereby preventing the fleas from reproducing and, in addition, keeping the habitat of dogs and cats permanently free from fleas.

It has been found that by administering to dogs or cats orally or parenterally or by implant a larvicidally or ovicidally effective amount of a flea growth inhibiting benzoylurea, the reinfestation of dogs and cats by fleas can be drastically reduced or completely prevented.

It is known that some benzoylurea inhibit or completely suppress the further development of juvenile stages; however, this activity has always been observed when the active ingredient is applied direct to the parasites. In connection with the present invention, it is surprising, however, that the full activity is still achieved even when the active ingredient is administered to the host animal in relatively low concentrations and it reaches, in an indirect way, the adult flea via the blood ingested and, additionally, the flea larvae (the actual target) when they feed upon the feces excreted by the adult fleas. By killing merely the adult fleas, which has so far been the objective of methods of control, the host animal is freed from fleas for a short time only. It has been found that fleas can only be effectively controlled if the development of new flea populations from the flea eggs is successfully prevented.

Target pests may be exposed to the benzoylureas in two ways. The benzoylurea is ingested in the blood meal by adult insects and pass from adults to the egg where they are effective. Death may occur at the egg, larval, or pupal stage. Research on fleas indicates reduced egg production, high larval mortality and inability of adults to enclose from the pupal case. In addition to transmission to the egg, larval fleas are exposed when they feed upon feces excreted by adult fleas. Flea feces contain large amounts of undigested blood taken from the host and serve as a protein source for the developing flea.

Accordingly, the present invention embraces two aspects; namely the above-described method of preventing dogs and cats from being reinfested by fleas, and, at the same time, the suppression of the propagation of fleas, or to put it more precisely, a method of preventing the propagation of fleas, comprising the step of providing the fleas with nutrient blood which contains an effective amount of at least one of the benzoylureas. This method also includes the aspect that the nutrient blood is provided to the fleas by feeding an effective amount of one of the benzoylurea to a host dog or a host cat and allowing the fleas to feed on this circulating blood.

Flea growth inhibiting benzoylurea derivatives, which are also known as "dimiloids", are described in, for example, DE-OS-2,123,236; DE-OS-2,601,780; DE-OS-3,240,975; EP-72,438 and EP-42,533.

Compounds of this class and suitable for use in the method of the present invention are the following compounds of formula I

wherein $R_1$ is unsubstituted or substituted phenyl, naphthyl, pyridyl, pyridazinyl, pyrimidinyl or pyrazinyl, $R_2$ is hydrogen or $C_1-C_6$alkyl, $R_3$ is

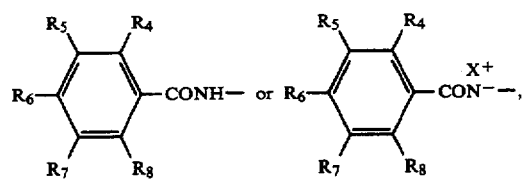

$R_4$ to $R_8$ are each independently hydrogen, halogen, $C_1-C_6$-alkyl, $C_1-C_6$haloalkyl, $C_1-C_6$alkoxy, $C_1-C_6$-haloalkoxy or $C_1-C_6$alkylthio, and $X^-$ is an inorganic or organic cation, suitable inorganic cations being alkali metal and alkaline earth metal cations and organic cations being characterized by the group

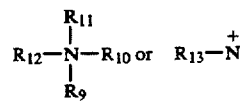

in which formulae, $R_9$ to $R_{12}$ are each independently hydrogen, $C_1$-$C_{20}$alkyl, benzyl, or phenyl and $R_{13}$ is hydrogen or $C_1$-$C_{20}$alkyl e.g. $H_4N^+$, $(CH_3)_4N^+$, $(C_2H_5)_4N^+$, $(n$-$C_3H_7)_4N^+$, $(i$-$C_3H_7)_4N^+$, $(n$-$C_4H_9)_4N^+$,

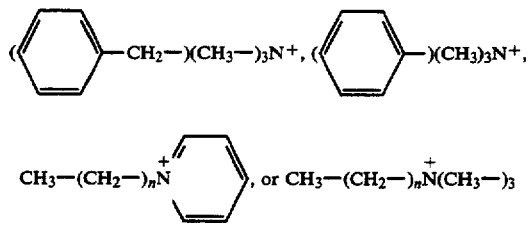

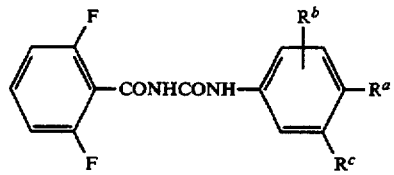

n being a value from 8 to 15.

Particularly preferred are benzoylurea of the formula:

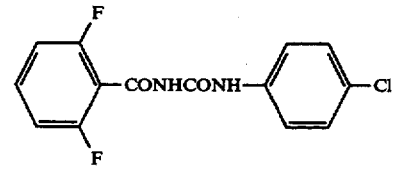 (II)

wherein:

$R^a$ is hydrogen; chloro; bromo; fluoro; methyl; trifluoromethyl; trifluoromethoxy; 2-chloro-1,1,2-trifluoroethoxy; 2-bromo-1,1,2-triflouroethoxy; 1,1,2,2-tetrafluoroethoxy; or 1,1,2,3,3,3-hexafluoroprop-1-oxy;

$R^b$ is hydrogen or chloro; and $R^c$ is hydrogen; chloro; 5-trifluoromethylpyrid-2-yloxy; or 3-chloro-5-trifluoromethylpyrid-2-yloxy;

at least one of $R^a$ and $R^c$ being other than hydrogen.

Preferred subgroups are those in which one of $R^a$ and $R^b$ is an ether group. Thus a first preferred subgroup are benzoylureas of Formula II in which $R^a$ is hydrogen, methyl, or chloro; $R^b$ is hydrogen; and $R^c$ is 5-trifluoromethylpyrid-2-yloxy or 3-chloro-5-trifluoromethylpyrid-2-yloxy. A second preferred subgroup are benzoylureas of Formula II in which $R^a$ is 2-chloro-1,1,2-trifluoromethoxy, 2-bromo-1,1,2-trifluoromethoxy; 1,1,2,2-tetrafluoroethoxy; or 1,1,2,3,3,3-hexafluoroprop-1-oxy; $R^b$ is chloro; and $R^c$ is chloro, that is an N-(2,6-difluorobenzoyl)-N'-(3,6-dichloro-4-$R^a$-phenyl)urea or N-(2,6-difluorobenzoyl)-N'-(3,5-dichloro-4-$R^a$-phenyl)urea.

Representative examples of particularly preferred individual compounds are:

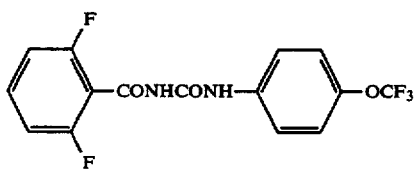 (a)

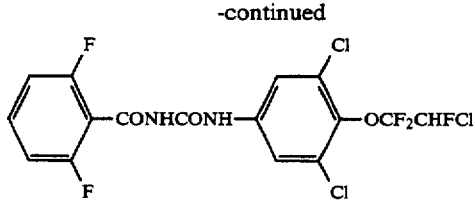 (b)

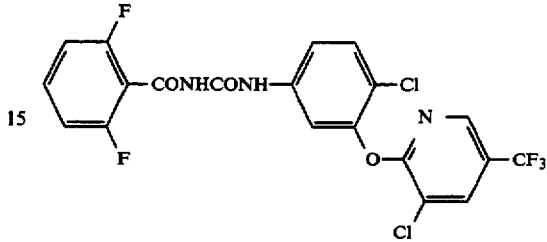 (c)

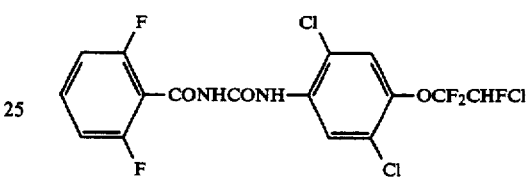 (d)

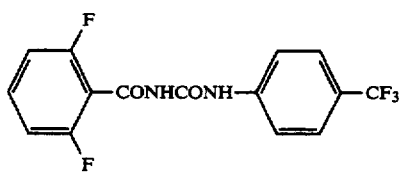 (e)

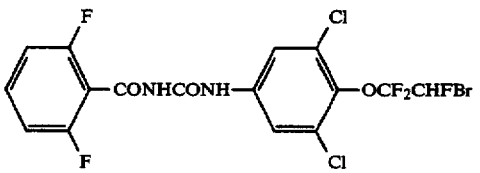 (f)

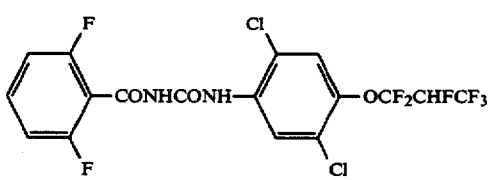 (g)

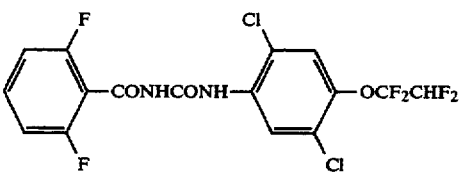 (h)

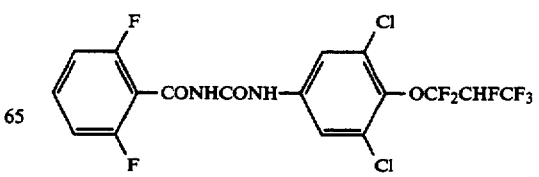 (i)

(j)

-continued

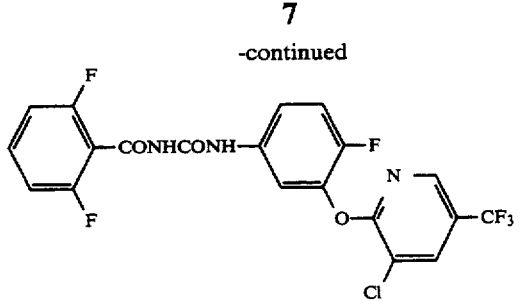
(k)

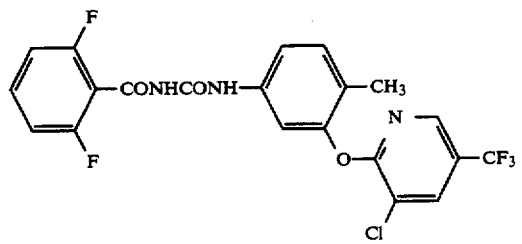
(l)

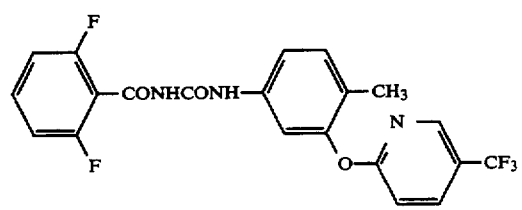
(m)

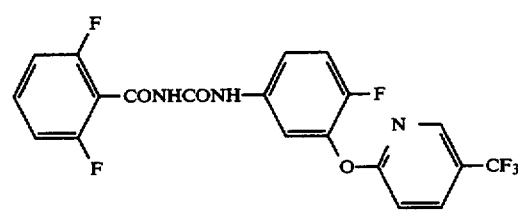
(n)

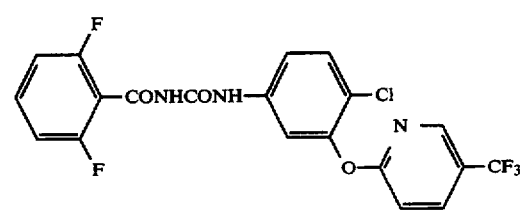
(o)

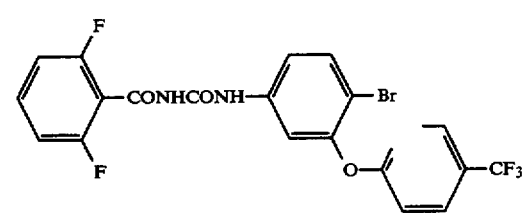
(p)

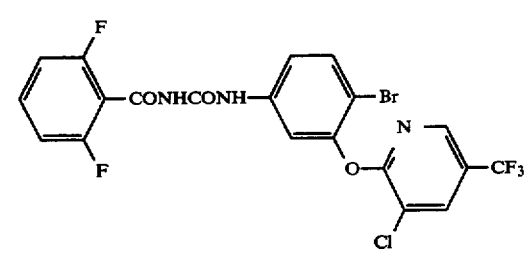
(q)

It is an essential feature of the present invention that the active benzoylurea is administered in such a manner that it can be ingested by the adult sucking flea with the circulating blood of the host animal and can then exhibit activity against the juvenile flea stages. In accordance with the present invention, this is achieved with several forms of application, e.g. by administering a formulated active ingredient orally. In this case, the term "formulated" means in the form of a powder, a tablet, a granulate, a capsule, an emulsion, a foam, etc. The preparation does not necessarily have to be administered to the animal direct; it may be convenient to mix it with the animal's feed.

Oral application can be in the form of tablets, capsules, lick-stones, bolus, drinking water, or granules. Parenteral administration can be accomplished by means of injection, implantation, or transdermal application.

In addition to containing adjuvants conventionally employed in the art of formulation, the compositions to be administered orally may of course contain further additives which stimulate voluntary ingestion by the animal, e.g. suitable scents or flavorings.

Owing to its simplicity, oral application is one of the preferred objects of the present invention. A further mode of application is parenteral application, e.g. by subcutaneous, intravenous or intramuscular injection or by means of a sustained action preparation in the form of an implant or other depot formulation.

Methods of oral application include but are not limited to compounds premixed in dog and cat food, fed in biscuits or treats, chewable tablets, water-dissolvable capsules or tablets, water-soluble compounds applied with a dropper into water or materials applied in any form onto dog food. Implant include any device applied into the animal for release of compounds to control fleas.

Percutaneous administration is conveniently accomplished by subcutaneous, dermal, intramuscular and even intravenous application of the injectable formulation. Conventional needle-type injection devices as well as needle-less air-blast injection devices can be used.

It is possible to delay or sustain the permeation of the active ingredient through the animal's living tissues by proper formulation. For example, a very insoluble compound may be used. In this case, the slight solubility of the compound causes sustained action because the body fluids of the animal can dissolve only a small amount of the compound at any one time. Sustained action of the active ingredient can also be obtained by formulating the compound in a matrix which will physically inhibit dissolution. The formulated matrix is injected into the body where it remains as a depot from which the compound slowly dissolves.

Matrix formulations, now known in the art, are formulated in waxy semisolids such as vegetable waxes and high molecular weight polyethylene glycols.

Very effective sustained action is obtained by introducing into the animal or implant containing one of the active ingredients. Such implants are now well known in veterinary art and are usually made of a silicone-containing rubber. The active ingredient is dispersed through a solid rubber implant or is contained inside a hollow implant. Care must be taken to choose an active ingredient which is soluble in the rubber form which the implant is made, since it is dispersed by first dissolving in the rubber and then leaching out of the rubber into the body fluids of the treated animal.

The rate at which active ingredient is released from an implant, and hence the length of time during which the implant remains effective, is controlled with good accuracy by the proper adjustment of the concentration of the compound in the implant, the external area of the implant, and the formulation of the polymer from which the implant is made.

Administration of the active ingredient by means of an implant is a further particularly preferred embodiment. Such administration is highly economical and efficacious because a properly designed implant maintains a constant concentration of the compound in the tissues of the host animal. An implant can be designed to supply compound for several months and is easily inserted in the animal. No further handling of the animal or concern over the dosage is necessary after the insertion of the implant.

The formulation of veterinary additives in animal feed is an extremely well-known art. It is usual to formulate the compound first as a premix in which the active ingredient is dispersed in a liquid or particulate solid carrier. The premix may conveniently contain from about 1 to 800 g of compound per kilogram, depending on the desired concentration in the feed. As is known in the art, many active -ingredients can be hydrolyzed or degraded by constituents of animal feed. Such compounds are routinely formulated in protective matrices such as gelatin before addition to the premix.

Therefore, the present invention is also directed to a method of systemically preventing the reinfestation of dogs and cats by fleas, which method comprises administering to said host animals orally, parenterally or by implant a larvicidally or ovicidally effective amount of a flea growth inhibiting benzoylurea derivative.

The present invention also relates to a method of preventing the propagation of fleas, comprising the step of providing the fleas with nutrient circulating blood which contains an effective amount of a flea growth inhibiting benzoylurea or more specifically the present invention also relates to the method of preventing the propagation of fleas by feeding an effective amount of a flea growth inhibiting substance, as characterized above, to the host animal and letting the fleas feed thereon.

The benzoylurea is conveniently applied in a dose of 0.01 to 800, preferably 0.5 to 200, most preferably 1 to 30, mg/kg body eight, based on the host animal, with oral administration being preferred. A good dose for regular administration is in general in the range from 1 to 100 mg/kg body weight of the host animal. Doses are usefully regularly repeated at daily to weekly intervals.

The total dose of the benzoylurea can vary from one genus of animal to the other and can even vary within the same genus since said dose depends, inter alia, on the weight and constitution of the animal.

In the method of the present invention, the benzoylurea normally is not applied in pure form, but preferably in the form of a composition which, in addition to containing the active ingredient, contains application promoters which are tolerated by the host animal. Naturally, in addition to the method of controlling juvenile development stages in accordance with the present invention, the adult fleas may also be controlled by conventional methods. However, these additional measures are not absolutely necessary.

The composition to be applied in the method of this invention usually contains 0.1 to 99% by weight, preferably 0.1 to 95% by weight, of the benzoylurea, and 99.9 to 1% by weight, preferably 0.1 to 25% by weight, of a solid or liquid non-toxic adjuvant, including 0 to 25% by weight, preferably 0.1 to 25% by weight, of a non-toxic surfactant.

Whereas commercial products are preferably formulated as concentrates, the end user will normally employ dilute formulations.

The compositions may also contain further ingredients, such as stabilizers, antifoams, viscosity regulators, binders, tackifiers as well as other active ingredients for obtaining special effects.

Materials known from veterinary practice as being suitable for being administered orally, parenterally or by implant may be employed as formulation assistants. A number of examples are cited below.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatine, tragacanth, methylcellulose and/or, if desired, disintegrators, such as the above-mentioned starches, also carboxymethyl starch, crosslinked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores can be provided with suitable coatings that may be resistant to gastric juices, e.g. concentrated sugar solutions which may contain gum arabic, talc, polyvinylpyrrolidone, polyethylene glycol and/or titanium dioxide, or lacquer in suitable organic solvents or solvent mixtures or, for the production of coatings that are resistant to gastric juices, solutions of suitable cellulose preparations, such as acetylcellulose phthalate or hydroxypropylmethylcellulose phthalate. Colorings, flavorings or pigments can be added to the tablets or dragée coatings, for example, for identification purposes or to indicate different dose of active ingredients.

Further orally administrable preparations are dry-filled capsules consisting of gelatine and also soft, sealed capsules consisting of gelatine and a plasticizer, such as glycerol or sorbitol. The dry-filled capsules may contain the active ingredient in the form of a granulate, for example in admixture with fillers, such as lactose, binders, such as starches, and/or glidants, such as talc or magnesium stearate, and optionally stabilizers. In soft capsules, the active ingredient is preferably dissolved or suspended in suitable liquids, such as fatty oils, paraffin oil or liquid polyethylene glycols, it being possible also to add stabilizers. Preferred are, inter alia, capsules that can be easily bitten through or swallowed without being chewed.

Especially suitable for parenteral administration are aqueous solutions of an active ingredient in water-soluble form, for example a water-soluble salt, also suspensions of the active ingredient, sch as corresponding oily injection suspensions, e.g. suitable lipophilic solvents or vehicles, such as fatty oils, for example sesame oil, or synthetic fatty acid esters, for example ethyl oleate, or triglycerides, or aqueous injection suspensions that contain viscosity-increasing substances, for example sodium carboxymethylcellulose, sorbitol and/or dextran, and, optionally, also stabilizers.

The preparations of the present invention can be manufactured in a manner known per se, for example by means of conventional mixing, granulating, confectioning, dissolving or lyophilizing processes. For example, pharmaceutical preparations for oral administration can be obtained by combining the active ingredient with solid carriers, optionally granulating a resultant mixture, and processing the mixture or granulate, if desired or necessary after the addition of suitable adjuncts, to form tablets or dragée cores.

The following Examples illustrate the invention described hereinbefore, but do not limit its scope in any way. In these examples, the active ingredient can include any of N-(2,6-difluorobenzoyl)-N'-[3-(3-chloro-5-trifluoromethylpyrid-2-yloxy)-4-bromophenyl]urea, N-(2,6-difluorobenzoyl)-N'-[3-(3-chloro-5-trifluoromethylpyrid-2-yloxy)-4-methylphenyl]urea, N-(2,6-difluorobenzoyl)-N'-[3-(3-chloro-5-trifluoromethyl-pyrid-2-yloxy)-4-chlorophenyl]urea, N-(2,6-difluorobenzoyl)-N'-[3-(3-chloro-5-trifluoromethylpyrid-2-yloxy)-4-fluorophenyl]-urea, N-(2,6-difluorobenzoyl)-N'-[3-(5-trifluoromethylpyrid-2-yloxy)-4-bromophenyl]urea, N-(2,6-difluorobenzoyl)-N'-[3-(5-trifluoromethylpyrid-2-yloxy)-4-methylphenyl]urea, N-(2,6-difluorobenzoyl)-N'-[3-(5-trifluoromethylpyrid-2-yloxy)-4-chlorophenyl]urea, N-(2,6-difluorobenzoyl)-N'-[3-(5-trifluoromethylpyrid-2-yloxy)-4-fluorophenyl]urea, N-(2,6-difluorobenzoyl)-N'-[3,5-dichloro-4-(2-chloro-1,1,2-trifluoroethoxy)phenyl]urea, N-(2,6-difluorobenzoyl)-N'-[3,6-dichloro-4-(2-chloro-1,1,2-trifluoroethoxy)phenyl]urea, N-(2,6-difluorobenzoyl)-N'-[3,5-dichloro-4-(1,1,2,3,3,3-hexafluoroprop-2-oxy)-phenyl]-urea, N-(2,6-difluorobenzoyl)-N'-[3,6-dichloro-4-(1,1,2,3,3,3-hexafluoroprop-1-oxy)phenyl]-urea, N-(2,6-difluorobenzoyl)-N'-[3,5-dichloro-4-(2-bromo-1,1,2-trifluoroethoxy)phenyl]urea, N-(2,6-difluorobenzoyl)-N'-[3,6-dichloro-4-(2-bromo-1,1,2-trifluoroethoxy)phenyl]urea, N-(2,6-difluorobenzoyl)-N'-[3,5-dichloro-4-(1,1,2,2-tetrafluoroethoxy)phenyl]urea, and N-(2,6-difluorobenzoyl)-N'-[3,6-dichloro-4-(1,1,2,2-tetrafluoroethoxy)phenyl]urea.

EXAMPLE 1

Tables containing 25 mg of active ingredient can be manufactured as follows:

| Constituents (for 1000 tablets) | |
| --- | --- |
| active ingredient | 25.0 g |
| lactose | 100.7 g |
| wheat starch | 7.5 g |
| polyethylene glycol (mol. wt. 6000) | 5.0 g |
| talc | 5.0 g |
| magnesium stearate | 1.8 g |
| demineralized water | q.s |

Manufacture

All the solid ingredients are first forced through a sieve having a mesh width of 0.6 mm. Then the active ingredient, the lactose, the talc, the magnesium stearate and half of the starch are mixed. The other half of the starch is suspended in 40 ml of water and this suspension is added to a boiling solution of the polyethylene glycol in 100 ml of water. The resulting starch paste is added to the main batch and the mixture, if necessary with the addition of water, is granulated. The granulate is dried overnight at 35° C., forced through a sieve having a mesh width of 1.2 mm and pressed to form tablets having a diameter of approximately 6 mm that are concave on both sides.

EXAMPLE 2

Tablets containing 0.02 g of active ingredient are manufactured as follows:

| Composition | |
| --- | --- |
| active ingredient | 200.00 g |
| lactose | 290.80 g |
| potato starch | 24.70 g |
| stearic acid | 10.00 g |
| talc | 200.00 g |
| magnesium stearate | 2.50 g |
| colloidal silica | 32.00 g |
| ethanol | q.s. |

A mixture of the active ingredient, the lactose and 194.70 g of the potato starch is moistened with an ethanolic solution of the stearic acid and granulated through a sieve. After drying, the remainder of the potato starch, the talc, the magnesium, and the colloidal silica are admixed and the mixture is pressed to form 0.1 g tablets which, if desired, can be provided with breaking grooves for finer adjustment of the dosage.

EXAMPLE 3

Capsules containing 0.025 g of the active ingredient can be manufactured as follows:

| Composition (for 1000 capsules) | |
| --- | --- |
| active ingredient | 25.00 g |
| lactose | 249.00 g |
| gelatine | 2.00 g |
| corn starch | 10.00 g |
| talc | 15.00 g |
| water | q.s. |

The active ingredient is mixed with the lactose and the mixture is moistened uniformly with an aqueous solution of the gelatine and granulated through a sieve having a mesh width of 1.2–1.5 mm. The granulate is mixed with dried corn starch and the talc is introduced in portions of 300 mg into hard gelatine capsules (size 1).

EXAMPLE 4

Premix (Feed Additive)

0.25 parts by weight of active ingredient and
4.75 parts of secondary calcium phosphate, or China clay, aerosol or carbonate or line are homogeneously mixed with
95 parts of an animal feed.

EXAMPLE 5

Injection Solution 8 parts by weight active ingredient
3.6 parts of acetic acid
88.4 parts of water for injection The acetic acid and the water are added to the active ingredient and the mixture is stirred until everything has dissolved. The solution is then filtered and sterilized by a suitable method. pH of the solution: 5.0.

EXAMPLE 6

Emulsifiable Concentrate 20 parts of active ingredient are mixed with 20 parts of emulsifier, e.g. a mixture of alkylarylpolyglycol ether with alkylaryl sulphonates, and 60 parts of solvent until the solution is completely homogeneous.

By diluting this concentrate with water it is possible to obtain an emulsion of the desired concentration.

EXAMPLE 7

Solutions (For Dilution With Drinking Water)

15% active ingredient in 2,2-dimethyl-4-hydroxymethyl1-1,3-dioxolane

10% active ingredient in diethylene glycol monethyl ether

10% active ingredient in polyethylene glycol (mol. wt. 300)

5% active ingredient in glycerol

EXAMPLE 8

Soluble Powder 25 parts of active ingredient
1 part of sodium lauryl sulfate
3 parts of colloidal silica
71 parts of urea The constituents are mixed and the mixture is finely ground in a suitable mill.

Other biocidal active ingredients or agents which are inert towards the active ingredients and acceptable to the animals to be treated, or mineral salts or vitamins can be admixed to the compositions described.

In a manner analogous to that described in the formulation Examples 1 to 8, it is possible to manufacture corresponding preparations containing a compound of the classes (a), (b) or (c) as defined above.

What is claimed is:

1. A method of suppressing flea reinfestation in the coat of a host cat or dog which comprises providing to the circulating blood of the host through oral or parenteral administration or through implantation, an amount of a benzoylurea which, when ingested by an adult flea infesting said host and feeding on said blood, is nonlethal to the ingesting adult flea but which inhibits, at a site other than on the host, the development of juvenile stages of progeny of the ingesting adult flea, said benzoylurea having the formula:

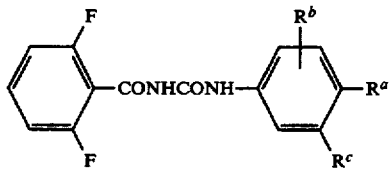

wherein:
$R^a$ is hydrogen; chloro; bromo; fluoro; methyl; trifluoromethyl; trifluoromethoxy; 2-chloro-1,1,2-trifluoroethoxy; 2-bromo-1,1,2-triflouroethoxy; 1,1,2,2-tetrafluoroethoxy; or 1,1,2,3,3,3-hexafluoroprop-1-oxy;

$R^b$ is hydrogen or chloro; and $R^c$ is hydrogen; chloro; 5-trifluoromethylpyrid-2-yloxy; or 3-chloro-5-trifluoromethylpyrid-2-yloxy;

at least one of $R^a$ and $R^c$ being other than hydrogen.

2. The method according to claim 1 in which in said benzoylurea $R^a$ is 2-chloro-1,1,2-trifluoroethoxy, 2-bromo-1,1,2-trifluoroethoxy; 1,1,2,2-tetrafluoroethoxy; or 1,1,2,3,3,3-hexafluoroprop-1-oxy; $R^b$ is chloro; and $R^c$ is chloro.

3. The method according to claim 2 wherein said benzoylurea is N-(2,6-difluorobenzoyl)-N'-(3,6-dichloro-4-$R^a$-phenyl)urea in which $R^a$ is 2-chloro1,1,2-trifluoroethoxy, 2-bromo-1,1,2-trifluoroethoxy; 1,1,2,2-tetrafluoroethoxy; or 1,1,2,3,3,3-hexafluoroprop-1-oxy.

4. The method according to claim 3 wherein said benzoylurea is N-(2,6-difluorobenzoyl)-N'-(3,5-dichloro-4-$R^a$-phenyl)urea in which $R^a$ is 2-chloro-1,1,2-trifluoroethoxy, 2-bromo-1,1,2-trifluoroethoxy; 1,1,2,2-tetrafluoroethoxy; or 1,1,2,3,3,3-hexafluoroprop-1-oxy.

5. The method according to claim 1 wherein said benzoylurea is administered orally.

6. The method according to claim 5 wherein the amount of said benzoylurea administered is from 0.01 to about 800 mg per kg of body weight.

7. The method according to claim 6 wherein the amount of said benzoylurea administered is from 1 to about 30 mg per kg of body weight.

8. The method according to claim 6 wherein the amount of said benzoylurea administered is from 0.5 to about 200 mg per kg of body weight.

9. The method according to claim 5 in which said benzoylurea is N-(2,6-difluorobenzoyl)-N'-[3,5-dichloro-4-(2-chloro-1,1,2-trifluoro-1-ethoxy)phenyl-]urea.

10. The method according to claim 5 in which said benzoylurea is N-(2,6-difluorobenzoyl)-N'-[3,6-dichloro-4-(2-chloro-1,1,2-trifluoro-1-ethoxy)phenyl-]urea.

11. The method according to claim 5 in which said benzoylurea is N-(2,6-difluorobenzoyl)-N'-[3,5-dichloro-4-(1,1,2,3,3,3-hexafluoroprop-1-oxy)phenyl]-urea.

12. The method according to claim 5 in which said benzoylurea is N-(2,6-difluorobenzoyl)-N'-[3,6-dichloro-4-(1,1,2,3,3,3-hexafluoroprop-1-oxy)phenyl]-urea.

13. The method according to claim 5 in which said benzoylurea is N-(2,6-difluorobenzoyl)-N'-[3,5-dichloro-4-(2-bromo-1,1,2-trifluoro-1-ethoxy)phenyl-]urea.

14. The method according to claim 5 in which said benzoylurea is N-(2,6-difluorobenzoyl)-N'-[3,6-dichloro-4-(2-bromo-1,1,2-trifluoroethoxy)phenyl]urea.

15. The method according to claim 5 in which said benzoylurea is N-(2,6-difluorobenzoyl)-N'-[3,5-dichloro-4-(1,1,2,2-tetrafluoroethoxy)phenyl]urea.

16. The method according to claim 5 in which said benzoylurea is N-(2,6-difluorobenzoyl)-N'-[3,6-dichloro-4-(1,1,2,2-tetrafluoroethoxy)phenyl]urea.

17. A method of suppressing flea reinfestation in the coat of a host cat or dog which comprises providing to the circulating blood of the host, through oral or parenteral administration or through implantation, an amount of a benzoylurea which, when ingested by an adult flea infesting said host and feeding on said blood, is nonlethal to the ingesting adult flea but which inhibits, at a site other than on the host, the development of juvenile stages of progeny of the ingesting adult flea, said benzoylurea having the formula:

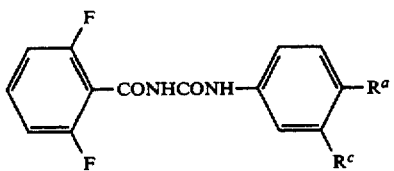

wherein:

$R^a$ is hydrogen, methyl, or chloro and $R^c$ is 5-trifluoromethylpyrid-2-yloxy or 3-chloro-5-trifluoromethylpyrid-2-yloxy.

18. The method according to claim 17 wherein said benzoylurea is administered orally.

19. The method according to claim 18 in which said benzoylurea is N-(2,6-difluorobenzoyl)-N'-[3-(3-chloro-5-trifluoromethylpyrid-2-yloxy)-4-bromophenyl]urea.

20. The method according to claim 18 in which said benzoylurea is N-(2,6-difluorobenzoyl)-N'-[3-(3-chloro-5-trifluoromethylpyrid-2-yloxy)-4-methylphenyl]urea.

21. The method according to claim 18 in which said benzoylurea is N-(2,6-difluorobenzoyl)-N'-[3-(3-chloro-5-trifluoromethylpyrid-2-yloxy)-4-chlorophenyl]urea.

22. The method according to claim 18 in which said benzoylurea is N-(2,6-difluorobenzoyl)-N'-[3-(3-chloro-5-trifluoromethylpyrid-2-yloxy)-4-fluorophenyl]-urea.

23. The method according to claim 18 in which said benzoylurea is N-(2,6-difluorobenzoyl)-N'-[3-(5-trifluoromethylpyrid-2-yloxy)-4-bromophenyl]urea.

24. The method according to claim 18 in which said benzoylurea is N-(2,6-difluorobenzoyl)-N'-[3-(5-trifluoromethylpyrid-2-yloxy)-4-methylphenyl]urea.

25. The method according to claim 18 in which said benzoylurea is N-(2,6-difluorobenzoyl)-N'-[3-(5-trifluoromethylpyrid-2-yloxy)-4-chlorophenyl]urea.

26. The method according to claim 18 in which said benzoylurea is N-(2,6-difluorobenzoyl)-N'-[3-(5-trifluoromethylpyrid-2-yloxy)-4-fluorophenyl]urea.

* * * * *